(12) United States Patent
Lachance

(10) Patent No.: US 6,824,556 B1
(45) Date of Patent: Nov. 30, 2004

(54) THERAPEUTIC PAD SYSTEM FOR APPLYING A COOLANT TO AN AFFECTED BODY PART

(76) Inventor: Carol Stonebrook Lachance, 6327 8th Ave. North, St. Petersburg, FL (US) 33710

( * ) Notice: Subject to any disclaimer, the term of this patent is extended or adjusted under 35 U.S.C. 154(b) by 0 days.

(21) Appl. No.: 09/977,125

(22) Filed: Oct. 12, 2001

(51) Int. Cl.[7] .................................................. A61F 7/00
(52) U.S. Cl. ........................ 607/109; 607/108; 607/112
(58) Field of Search ......................... 607/46, 108, 109, 607/110, 111, 112, 114; D24/206, 207, 208

(56) References Cited

U.S. PATENT DOCUMENTS

| | | | | |
|---|---|---|---|---|
| 4,372,318 A | * | 2/1983 | Viesturs et al. ............. | 607/109 |
| D273,043 S | * | 3/1984 | Rusch ........................ | D24/207 |
| 5,215,080 A | * | 6/1993 | Thomas et al. ............. | 607/112 |
| 5,304,215 A | * | 4/1994 | MacWhinnie et al. ...... | 607/108 |
| 5,441,534 A | * | 8/1995 | MacWinnie et al. ........ | 607/108 |
| 5,507,794 A | * | 4/1996 | Allen .......................... | 607/112 |
| 5,823,984 A | * | 10/1998 | Silverberg .................... | 602/61 |
| D405,187 S | * | 2/1999 | Douglas ..................... | D24/208 |
| D405,188 S | * | 2/1999 | Evans ........................ | D24/208 |
| 6,093,202 A | * | 7/2000 | Dyken et al. ............... | 607/109 |
| 6,168,613 B1 | * | 1/2001 | Besse ......................... | 607/114 |
| 6,623,517 B1 | * | 9/2003 | DeLuisa et al. ............ | 607/109 |

* cited by examiner

Primary Examiner—Beverly M. Flanagan
(74) Attorney, Agent, or Firm—Edward P. Dutkiewicz

(57) ABSTRACT

A therapeutic pad system comprises an ice patch having a generally disc-shaped configuration. The ice patch has a circular generally parallel first and second walls fabricated of a plastic-vinyl material. A non-solid gel which is capable of being frozen, thawed and re-frozen a plurality of times is located within the space between the walls. A jacket is fabricated of a cloth material and has a generally disc shaped configuration with an interior panel and an exterior panel and a pocket there between for receiving the ice patch. Common stitching is over approximately the lower two-thirds of the jacket and the upper one-third forms an opening. Decorative indicia coupled to the exterior panel of the jacket.

4 Claims, 3 Drawing Sheets

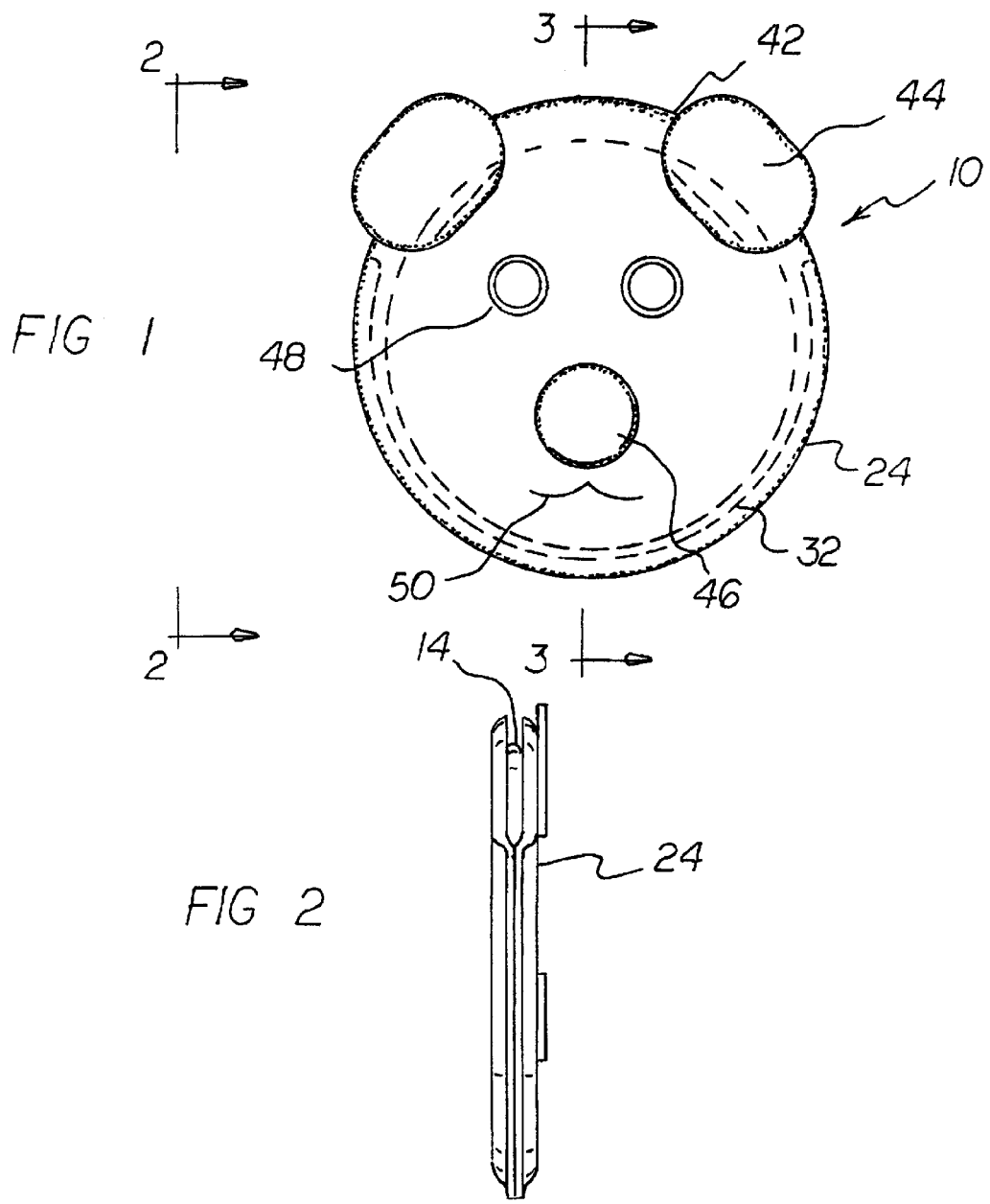

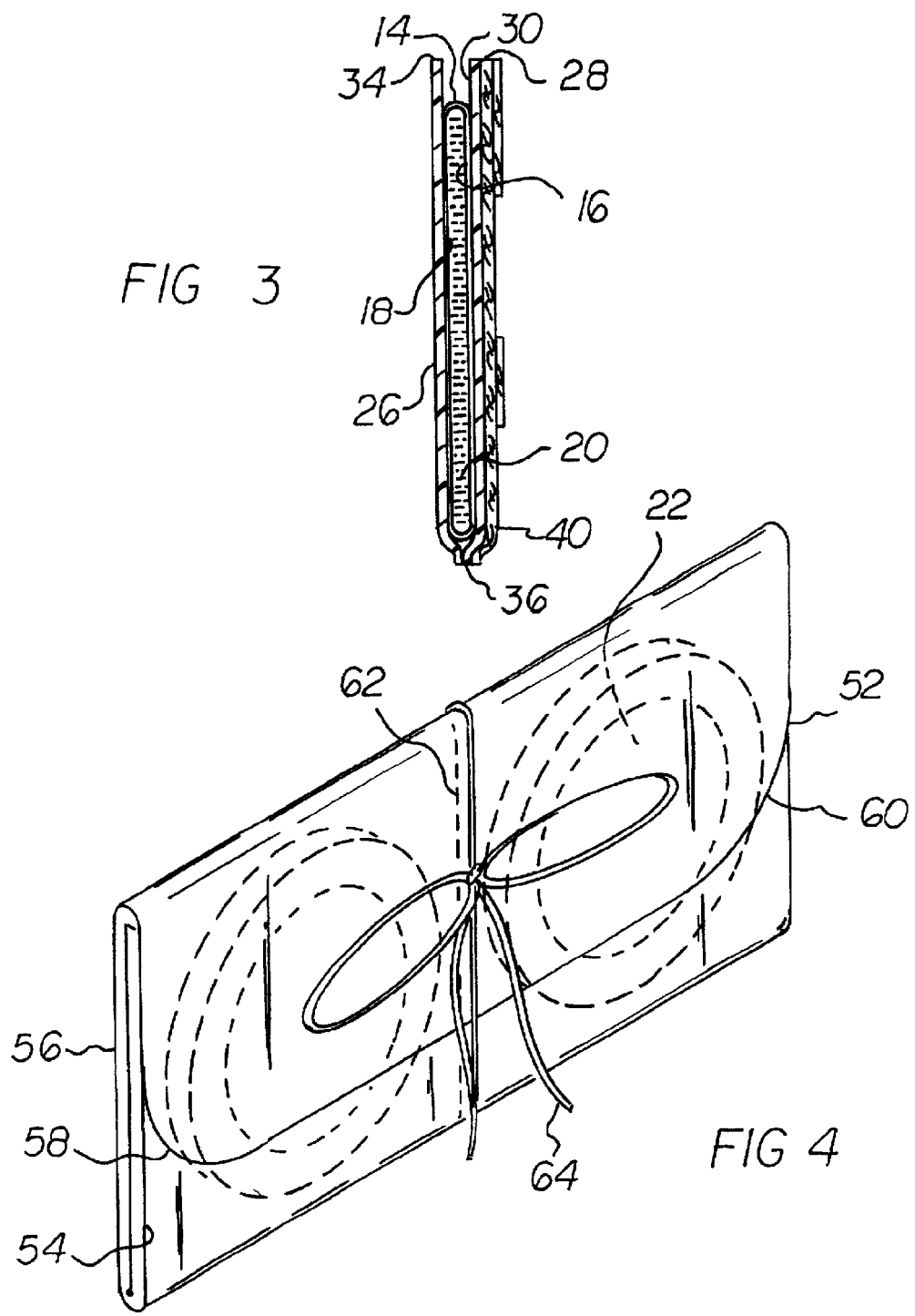

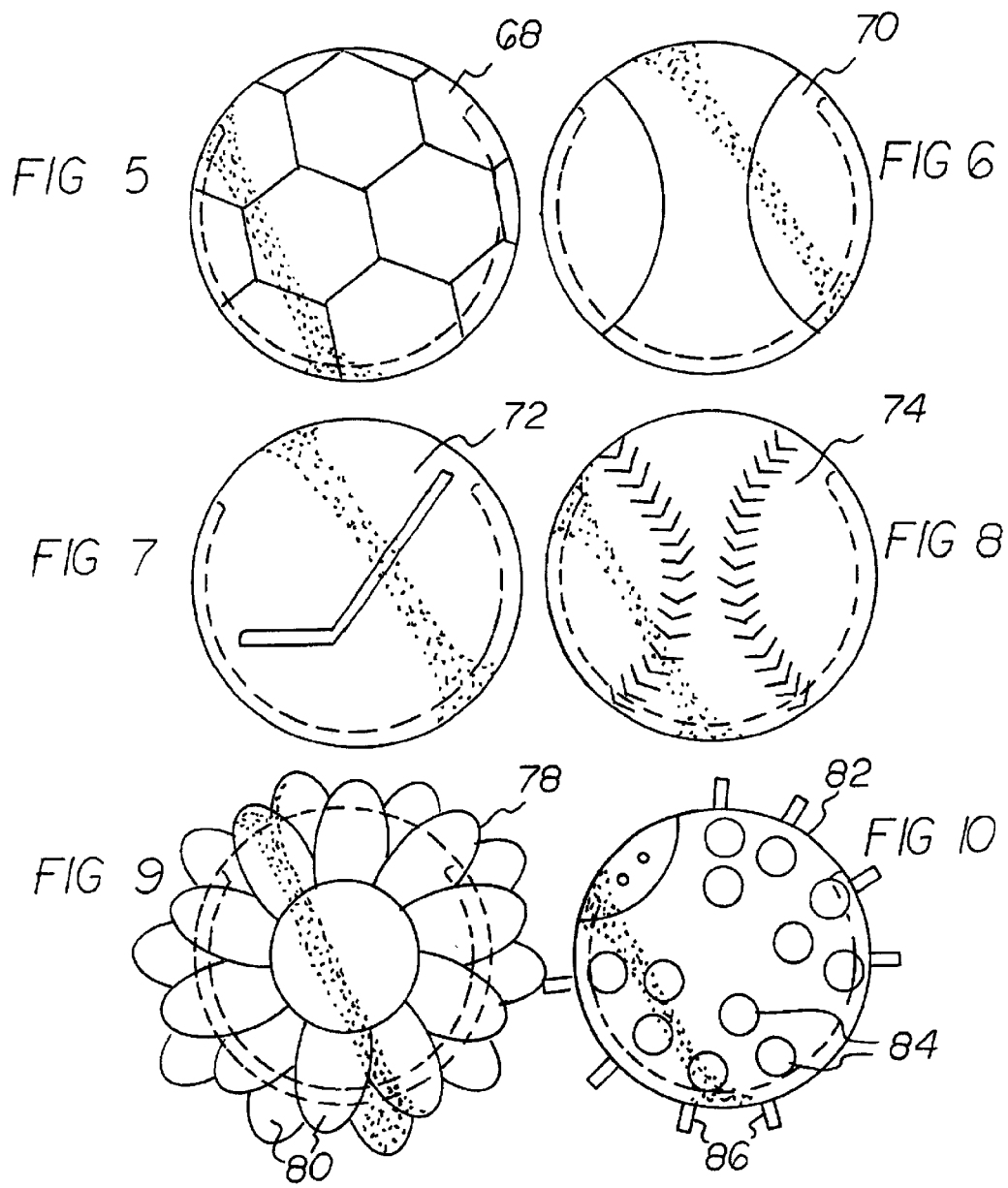

THERAPEUTIC PAD SYSTEM FOR APPLYING A COOLANT TO AN AFFECTED BODY PART

BACKGROUND OF THE INVENTION

1. Field of the Invention

The present invention relates to a therapeutic pad system and more particularly pertains to applying a coolant to an affected body part of a user to reduce pain, swelling or puffiness in a safe and efficient manner.

2. Description of the Prior Art

The use of therapeutic devices of known designs and configurations is known in the prior art. More specifically, therapeutic devices of known designs and configurations previously devised and utilized for the purpose of increasing the comfort of a patient through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 2,101,628 to Padelford discloses an ice bag. U.S. Pat. No. 3,768,485 to Linick discloses a treatment apparatus for the eye and orbit area. U.S. Pat. No. 4,243,041 to Paul discloses cold-pack goggles. U.S. Pat. No. 2,527,947 to Loos discloses an eye protector. U.S. Pat. No. 4,372,318 to Viesturs et al. discloses a thermal treatment device. Lastly, U.S. Pat. No. 4,783,866 to Simmons et al. discloses a therapy pillow with removable therapeutic gel pack.

While these devices fulfill their respective, particular objectives and requirements, the aforementioned patents do not describe a therapeutic pad system that allows applying a coolant to an affected body part of a user to reduce pain, swelling or puffiness in a safe and efficient manner.

In this respect, the therapeutic pad system according to the present invention substantially departs from the conventional concepts and designs of the prior art, and in doing so provides an apparatus primarily developed for the purpose of applying a coolant to an affected body part of a user to reduce pain, swelling or puffiness in a safe and efficient manner.

Therefore, it can be appreciated that there exists a continuing need for a new and improved therapeutic pad system which can be used for applying a coolant to an affected body part of a user to reduce pain, swelling or puffiness in a safe and efficient manner. In this regard, the present invention substantially fulfills this need.

SUMMARY OF THE INVENTION

In view of the foregoing disadvantages inherent in the known types of therapeutic devices of known designs and configurations now present in the prior art, the present invention provides an improved therapeutic pad system. As such, the general purpose of the present invention, which will be described subsequently in greater detail, is to provide a new and improved therapeutic pad system and method which has all the advantages of the prior art and none of the disadvantages.

To attain this, the present invention essentially comprises a therapeutic pad system for the application of a coolant to an affected body part of user to reduce pain, swelling or puffiness in a safe and efficient manner. First provided is an ice patch. The ice patch has a generally disc-shaped configuration with a diameter of about 3.5 inches. The patch has a circular first wall and a circular generally parallel second wall fabricated of a plastic-vinyl material. The first and second walls are coupled about their peripheries to form a space there between. A non-solid gel which is capable of being frozen, thawed and re-frozen a plurality of times is located within the space. Printed indicia in the form of a fruit or vegetable is provided on the exterior surface of one wall. A jacket fabricated of a cloth material is next provided. The jacket has a generally disc shaped configuration with a diameter of about 4 inches. The jacket has an interior panel and an exterior panel. The interior panel and the exterior panel form a pocket there between. Common stitching is provided approximately over the lower two thirds of the jacket. The upper one-third forms an opening for the movement of the ice patch to and from the pocket. The exterior panel is fabricated of a circular disc of a cloth lining interiorly and a circular disc of felt externally. The interior panel is fabricated of a mixture of natural and/or synthetic fiber staples, preferably Pellon. The internal diameter is slightly larger than the external diameter of the ice patch. Decorative indicia is provided. The indicia comprises two oval felt ears, a round felt nose, two round cloth eyes of liquid paint, and a mouth of liquid paint. The indicia is coupled exteriorly to the exterior panel of the jacket. Next provided is a carrying case. The carry case is fabricated of a heavy cloth material. The carrying case has a forward wall and an integral rearward wall coupled at their side edges. The rearward wall extends into a flap. The flap has a generally rectilinear configuration with radially concentric edges. The forward and rearward walls form a pocket there within with a line of stitching parallel with the side edges to form two pockets for receiving two jackets, each with an ice patch. Lastly, a tie is provided. The tie is fabricated of flexible material having a length of between about 12 and 24 inches. The tie is coupled at its center to the outer surface of the rearward wall to hold the flap to the carrying case when tied and to allow access to the jackets and ice patches when untied.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved therapeutic pad system which has all of the advantages of the prior art therapeutic devices of known designs and configurations and none of the disadvantages.

It is another object of the present invention to provide a new and improved therapeutic pad system which may be easily and efficiently manufactured and marketed.

It is further object of the present invention to provide a new and improved therapeutic pad system which is of durable and reliable constructions.

An even further object of the present invention is to provide a new and improved therapeutic pad system which is susceptible of a low cost of manufacture with regard to both materials and labor, and which accordingly is then susceptible of low prices of sale to the consuming public, thereby making such therapeutic pad system economically available to the buying public.

Even still another object of the present invention is to provide a therapeutic pad system for applying a coolant to an affected body part of a user to reduce pain, swelling or puffiness in a safe and efficient manner.

Lastly, it is an object of the present invention to provide a new and improved therapeutic pad system comprising an ice patch having a generally disc-shaped configuration. The ice patch has a circular generally parallel first and second walls fabricated of a plastic-vinyl material. A non-solid gel which is capable of being frozen, thawed and re-frozen a plurality of times is located within the space between the walls. A jacket is fabricated of a cloth material and has a generally disc shaped configuration with an interior panel and an exterior panel and a pocket there between for receiving the ice patch. Common stitching is over approximately the lower two-thirds of the jacket and the upper one-third forms an opening. Decorative indicia coupled to the exterior panel of the jacket.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of the therapeutic pad system constructed in accordance with the principles of the present invention.

FIG. 2 is a side elevational view taken along line 2—2 of FIG. 1.

FIG. 3 is a cross sectional view taken along line 3—3 of FIG. 1.

FIG. 4 is a perspective view of the therapeutic pad system shown in the prior figures.

FIGS. 5–10 are front elevational views of alternate embodiments of the invention.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved therapeutic pad system embodying the principles and concepts of the present invention and generally designated by the reference numeral 10 will be described.

The present invention, the therapeutic pad system 10 is comprised of a plurality of components. Such components in their broadest context include an ice patch, a jacket, and decorative indicia. Such components are individually configured and correlated with respect to each other so as to attain the desired objective.

First provided is an ice patch 14. The ice patch has a generally disc-shaped configuration with a diameter of about 3.5 inches. The patch has a circular first wall 16 and a circular generally parallel second wall 18 fabricated of a plastic-vinyl material. The first and second walls are coupled about their peripheries to form a space there between. A non-solid gel 20 which is capable of being frozen, thawed and re-frozen a plurality of times is located within the space. Printed indicia 22 in the form of a fruit or vegetable is provided on the exterior surface of one wall.

A jacket 24 fabricated of a cloth material is next provided. The jacket has a generally disc shaped configuration with a diameter of about 4 inches. The jacket has an interior panel 26 and an exterior panel 28. The interior panel and the exterior panel form a pocket 30 there between. Common stitching 32 is provided approximately over the lower two thirds of the jacket. The upper one-third forms an opening 34 for the movement of the ice patch to and from the pocket. The exterior panel is fabricated of a circular disc 36 of a cloth lining interiorly and a circular disc 40 of felt externally. The interior panel is fabricated of a mixture of natural and/or synthetic fiber staples, preferably Pellon. The internal diameter is slightly larger than the external diameter of the ice patch.

Decorative indicia 42 is provided. The indicia comprises two oval felt ears 44, a round felt nose 46, two round cloth eyes 48 of liquid paint, and a mouth 50 of liquid paint. The indicia is coupled exteriorly to the exterior panel of the jacket.

Next provided is a carrying case 52. The carry case is fabricated of a heavy cloth material. The carrying case has a forward wall 54 and an integral rearward wall 56 coupled at their side edges. The rearward wall extends into a flap 58. The flap has a generally rectilinear configuration with radially concentric edges 60. The forward and rearward walls form a pocket there within with a line of stitching 62 parallel with the side edges to form two pockets for receiving two jackets, each with an ice patch.

Lastly, a tie is provided. The tie is fabricated of flexible material having a length of between about 12 and 24 inches. The tie is coupled at its center to the outer surface of the rearward wall to hold the flap to the carrying case when tied and to allow access to the jackets and ice patches when untied.

In alternate embodiments of the invention, the indicia on the jacket may be a volley ball 68, a tennis ball 70, a hockey L: stick 72, a baseball 74, a flower 78 composed of felt pedals 80, or a lady bug 82 with liquid ink spots 84 and felt legs 86.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A therapeutic pad system for the application of a coolant to an affected body part of a user to reduce pain, swelling and puffiness in a safe and efficient manner comprising, in combination:

an ice patch having a generally disc-shaped configuration with a diameter of about 3.5 inches, the patch having a circular first wall and a circular generally parallel second wall fabricated of a plastic-vinyl material with the first and second walls coupled about their peripheries to form a space there between and with a non-solid gel which is capable of being frozen, thawed and re-frozen a plurality of times located within the space, the exterior surface of one wall having printed indicia in the form of a fruit or vegetable;

a jacket fabricated of a cloth material and having a generally disc shaped configuration with a diameter of about 4 inches with the jacket having an interior panel and an exterior panel with the interior panel and the exterior panel forming a pocket there between with common stitching approximately over the lower two thirds of the jacket and with the upper one-third forming an opening for the movement of the ice patch to and from the pocket, the exterior panel being fabricated of a circular disc of a cloth lining interiorly and a circular disc of felt externally, the interior panel being fabricated of a mixture of fiber staples having an internal diameter slightly larger than the external diameter of the ice patch;

decorative indicia comprising two oval felt ears and a round felt nose and two round cloth eyes of liquid paint and a mouth of liquid paint, the indicia coupled exteriorly to the exterior panel of the jacket;

a carrying case fabricated of a heavy cloth material having a forward wall and an integral rearward wall coupled at their side edges, the rearward wall extending into a flap, the flap having a generally rectilinear configuration with radially concentric edges, the forward and rearward walls forming a pocket there within with a line of stitching parallel with the side edges to form two pockets for receiving two jackets, each with an ice patch; and a tie fabricated of flexible material having a length of between about 12 and 24 inches, the tie being coupled at its center to the outer surface of the rearward wall to hold the flap to the carrying case when tied and to allow access to the jackets and ice patches when untied.

2. A therapeutic pad system comprising:

an ice patch having a generally disc-shaped configuration, the patch having a circular first wall and a circular generally parallel second wall fabricated of a plastic-vinyl material, a non-solid gel which is capable of being frozen, thawed and refrozen frozen a plurality of times located within the space between the walls, the ice patch being configured to be retained on an eye of a user by gravity;

a jacket fabricated of a cloth material and having a generally disc shaped configuration with an interior panel and an exterior panel and a pocket there between for receiving the ice patch and including common stitching approximately over the lower two-thirds of the jacket and with the upper one-third forming an opening; and decorative indicia coupled to the exterior panel of the jacket.

3. The system as set forth in claim 2 and further including:

a carrying case fabricated of a heavy cloth material having a forward wall and an integral rearward wall coupled at their side edges, the rearward wall extending into a flap, the flap having a generally rectilinear configuration with radially cornered edges, the forward and rearward walls forming a pocket there within with a line of stitching parallel with the side edge to form two pockets for receiving two jackets, each with an ice patch, and a tie fabricated of flexible material having a length of between about 12 and 24 inches, the tie being coupled at its center to the outer surface of the rearward wall to hold the flap to the case when tied and to allow access to the jackets and ice patches when untied.

4. The system as set forth in claim 2 and further including indicia on one surface of the ice patch.

* * * * *